United States Patent [19]
Erneta et al.

[11] Patent Number: 5,854,383
[45] Date of Patent: Dec. 29, 1998

[54] ALIPHATIC POLYESTERS OF TRIMETHYLENE CARBONATE EPSILON-CAPROLACTONE AND GLYCOLIDE

[75] Inventors: Modesto Erneta, Princeton Junction; Idrish A. Vhora, Somerville, both of N.J.

[73] Assignee: Ethicon, Inc., Somerville, N.J.

[21] Appl. No.: 944,792

[22] Filed: Oct. 6, 1997

[51] Int. Cl.$^6$ .................................................. C08G 63/08
[52] U.S. Cl. .................. 528/354; 128/335.5; 528/357; 606/230
[58] Field of Search .................. 128/335.5; 528/354, 528/357; 606/230

[56] References Cited

U.S. PATENT DOCUMENTS

| | | | |
|---|---|---|---|
| 4,300,565 | 11/1981 | Rosensaft et al. | 128/335.5 |
| 5,252,701 | 10/1993 | Jarrett et al. | 528/354 |
| 5,403,347 | 4/1995 | Roby et al. | 606/230 |
| 5,431,679 | 7/1995 | Bennett et al. | 606/230 |
| 5,502,159 | 3/1996 | Liu et al. | 528/354 |

*Primary Examiner*—Terressa Mosley
*Attorney, Agent, or Firm*—Hal Brent Woodrow

[57] ABSTRACT

Absorbable, segmented copolymers of aliphatic polyesters based on lactone monomers glycolide, trimethylene carbonate and ε-caprolactone are described. The segmented copolymers exhibit a broad range of properties, especially high strength, low modulus and fast in vivo absorption, useful in a variety of medical devices. The copolymers of the present invention have such properties, making them useful in medical devices for plastic surgery indications.

14 Claims, No Drawings

ALIPHATIC POLYESTERS OF TRIMETHYLENE CARBONATE EPSILON-CAPROLACTONE AND GLYCOLIDE

FIELD OF THE INVENTION

This invention relates to polymers; in particular, polymers of aliphatic polyesters of trimethylene carbonate, ε-caprolactone, and glycolide, which are biocompatible, absorbable and well suited for the preparation of sutures.

BACKGROUND OF THE INVENTION

Synthetic absorbable biocompatible polymers are well known in the art. Such polymers are typically used to manufacture medical devices, which are implanted in body tissue and absorb over time. Synthetic absorbable biocompatible polymers include homopolymers, copolymers (random, block, segmented and graft) of monomers such as glycolic acid, glycolide, lactic acid, lactide, (d, ,l meso and mixtures thereof), ε-caprolactone, trimethylene carbonate and p-dioxanone. Numerous U.S. Patents describe these polymers including U.S. Pat. Nos. 5,431,679; 5,403,347; 5,314,989; 5,431,679; 5,403,347; and 5,502,159.

U.S. Pat. No. 5,252,701 (Jarrett et al.) describes copolymers composed of at least two different types of ester linkages. Jarrett suggests that ε-caprolactone or trimethylene carbonate plus a minor amount glycolide or lactide may be polymerized in the first stage of polymerization followed in a second stage polymerization comprised mostly of glycolide or lactide provides a segmented polymer architecture with a controllable and well defined segment length. These polymers are described as being suitable for a variety of medical or surgical devices.

U.S. Pat. No. 5,403,347 also describes a glycolide based block copolymer. The copolymer described in this patent consist of: 1) an A block of at least 50 mole percent glycolide which may be copolymerized with lactide, trimethylene carbonate, p-dioxanone and epsilon-caprolactone; and 2) a B block of p-dioxanone (1,4-dioxan-2-one) and trimethylene carbonate (1,3-dioxan-2-one).

U.S. Pat. No. 5,431,679 describes block copolymers of from about 50 to about 65 weight percent of a first block predominately consisting of glycolic acid ester units and another block which is of caprolactone and 1,3-dioxan-2-one.

Unfortunately, these patents do not recognize that especially flexible sutures could be manufactured from a copolymer of glycolic repeating units copolymerized with a random prepolymer predominately of trimethylene carbonate, glycolide and s-caprolactone repeating units.

Accordingly, what is needed in this art are novel polymer compositions which have high tensile strength but low modulus, useful as, for example, sutures in plastic surgical indications.

SUMMARY OF THE INVENTION

We have discovered absorbable, biocompatible, segmented polymers of trimethylene carbonate, ε-caprolactone and glycolide which provides a desirable combination of tensile strength and flexibility (low modulus). The polymers are composed of about 10 mole percent to about 80 mole percent of glycolic ester repeating units which have been copolymerized with a prepolymer of about 95 mole percent to about 30 mole percent of trimethylene carbonate, ε-caprolactone and glycolide wherein the weight percentage of trimethylene carbonate to ε-caprolactone to glycolide are respectively about 2 to about 40, about 2 to about 40 and about 2 to about 40 mole percent (based on the total mole of the polymer equaling 100 percent).

We have additionally discovered that by preparing segmented polymers of ε-caprolactone, trimethylene carbonate and glycolide by a process in which trimethylene carbonate, ε-caprolactone and glycolide monomers are reacted at low temperatures from about 100° C. to about 195° C. followed by reaction with glycolide at temperatures of about 160° C. to about 230° C., polymers of trimethylene carbonate, ε-caprolactone and glycolide can be formed with high tensile and knot fiber strength, which are extremely pliable (characterized by having a low Young's modulus). These polymers are especially well suited for making monofilaments sutures for plastic surgery indications.

Still yet a further aspect of the present invention is the polymer of the present invention which is a product of the process of the present invention.

The foregoing and other features and advantages of the invention will become more apparent from the following description and accompanying examples.

DETAILED DESCRIPTION OF THE INVENTION

In theory but in no way limiting the scope of the present invention it is believed that the polymers of the present invention have sequences or arrangements of repeating units. Since each repeating segment is composed of several monomers, the polymer has very few crystalline domains and consequently the degree of crystallinity (i.e., percent) of the polymer is low. This yields a structure where a few crystalline domains act as physical crosslinks between the amorphous regions of the polymer, yielding low modulus and high strength. In addition, since the polymers of the present invention have low modulus, when formed into a monofilament suture their handling and tissue pass through is better than absorbable braided sutures. Block polymers would have a much greater degree of crystallinity, creating a highly crystalline material, thereby yielding very stiff, high modulus devices, especially sutures, limiting their usefulness. In applications that require pliable monofilament sutures to reduce tissue damage, such as plastic surgery, the present polymers are far superior to the polymers disclosed in the prior art. The process of the present invention is a multi-step, one-reaction vessel, two-temperature process in which a prepolymer of ε-caprolactone-co-trimethylene carbonate-co-glycolide, formed at low temperatures of from about 100° C. to about 195° C., preferably 180° C. for about 2 to about 8 hours, then reacted with glycolide at temperatures from about 160° C. to about 230° C. to form polymers in which segments or sequences are composed of ε-caprolactone, trimethylene carbonate and glycolide, with additional glycolide repeating units at the end of the chain. These segmented polymers are soft, pliable materials with low Young's modulus. Generally the Young's modulus of these polymers will be less than 200,000 psi, preferably the modulus of these polymers will be less than 185,000 psi and more preferably the modulus will be in the range of from about 150,000 psi to about 50,000 psi.

More specifically, the segmented polymers composed of glycolide, ε-caprolactone, and trimethylene carbonate of the present invention are prepared by a process in which trimethylene carbonate, ε-caprolactone and glycolide monomers in the initial monomer feed of the polymer are reacted at low temperatures from about 100° C. to about 195° C., preferably about 160° C. to 190° C., for a sufficient time effective to cause polymerization, preferably about 1.5 to about 8 hours, followed by reaction with glycolide for about one-half to about 8 hours at higher temperatures of about 160° C. to about 230° C. for a sufficient time effective to cause polymerization, preferably about one-half hour to about 4 hours.

Furthermore, the segmented polymers composed of glycolide, trimethylene carbonate, and ε-caprolactone of the present invention will typically consist of about 10 mole percent to about 80 mole percent of repeating units of glycolide (including equivalent amounts of glycolic ester repeating units), more preferably about 40 mole percent to about 65 mole percent of repeating units of glycolide. In addition, the mole percentages of trimethylene carbonate to ε-caprolactone to glycolide are respectively about 2 to about 40; 2 to about 40 and about 2 to about 35, preferably about 10 to about 30, about 10 to about 30 and about 5 to about 15 mole percent. The prepolymer of trimethylene carbonate, ε-caprolactone and glycolide generally should have an inherent viscosity in the range of from about 0.6 dL/g to about 2 dL/g and preferably will have an inherent viscosity in the range of from about 0.8 dL/g to about 1.9 dL/g.

The polymers of the present invention will typically be synthesized in a ring opening polymerization. That is, the aliphatic lactone monomers are polymerized in the presence of an organometallic catalyst and an initiator at elevated temperatures. The organometallic catalyst is preferably tin based, e.g., stannous octoate, and is present in the monomer mixture at a molar ratio of monomer to catalyst ranging from about 10,000/1 to about 100,000/1. The initiator is typically an alkanol (including diols and polyols), a glycol, a hydroxyacid, or an amine, and is present in the monomer mixture at a molar ratio of monomer to initiator ranging from about 100/1 to about 5000/1. The polymerization is typically carried out at a temperature range from about 80° C. to about 240° C., preferably from about 100° C. to about 220° C., until the desired molecular weight and viscosity are achieved.

Additionally, a minor amount (less than 5, preferably less than 3 weight percent weight percent) of additional lactone monomers selected from the group consisting of p-dioxanone, delta-valerolactone, beta-butyrolactone, epsilon-decalactone, 2,5-diketomorpholine, pivalolactone, alpha-propiolactone, alpha-diethylpropiolactone, ethylene carbonate, ethylene oxalate, 3-methyl-1,4-dioxane-2,5-dione, 3,3-diethyl-1,4-dioxan-2,5-dione, gamma-butyrolactone, 1,4-dioxepan-2-one, 1,5-dioxepan-2-one, 6,6-dimethyl-dioxepan-2-one, 6,8-dioxabicycloctane-7-one and combinations of two or more thereof may be added to the either the prepolymer or with the addition of the glycolic ester repeating units of the polymer.

In one embodiment of the present invention the prepolymer of trimethylene carbonate, glycolide and ε-caprolactone is polymerized in a first polymerization. The polymerization is typically carried out at a temperature range from about 100° C. to about 190° C., preferably 180° C., for about 1.5 to about 8 hours, preferably 3 to 6 hours, yielding a trimethylene carbonate-co-ε-caprolactone-co-glycolide prepolymer. Then, glycolide monomer is added to the prepolymer and the temperature is raised to about 160° C. to about 230° C., preferably from about 180° C. to about 210° C. for about one-half hour to about 4 hours until the desired molecular weight and viscosity are achieved. Alternatively, the glycolide could be added slowly on in discrete multiple additions to the prepolymer to improve the mixing of the monomer with the prepolymer.

Under the above described conditions, the segmented polymers composed of glycolide, ε-caprolactone, and trimethylene carbonate, will typically have a weight average molecular weight of about 20,000 grams per mole to about 300,000 grams per mole, more typically about 40,000 grams per mole to about 200,000 grams per mole, and preferably about 60,000 grams per mole to about 150,000 grams per mole. These molecular weights provide an inherent viscosity between about 0.7 to about 4.0 deciliters per gram (dL/g), more typically about 1 to about 3.5 dL/g, and most preferably about 1 to about 3.0 dL/g as measured in a 0.1 g/dL solution of hexafluoroisopropanol (HFIP) at 25° C. Also, it should be noted that under the above described conditions, the residual monomer content will be less than about 5 weight percent.

The segmented polymers composed of glycolide, ε-caprolactone, and trimethylene carbonate will typically consist of about 10 mole percent to about 80 mole percent, more preferably about 40 mole percent to about 65 mole percent of glycolide repeating units. The limits lead to polymers with a desirable range of strength, stiffness and absorption profiles for use in a variety of biomedical applications. The lower limit yields polymers with a low degree of crystallinity, imparting a low modulus to fibers produced from these materials, and hence, excellent tissue pass through with less scaring (Table 4). The upper limit is the cut-off between forming a single phase polymer and a two phase blend of the terpolymer of the present invention and a homopolymer of poly(glycolide) as well as imparting a BSR profile conducive to use in plastic surgery (i.e., BSR less than 25 percent at 3 weeks).

Articles such as medical devices are molded from the segmented polymers of the present invention by use of various injection and extrusion molding equipment equipped with dry nitrogen atmospheric chamber(s) at temperatures ranging from about 140° C. to about 220° C., more preferably 180° C. to about 220° C., with residence times of about 2 to about 30 minutes, more preferably about 2 to about 10 minutes.

The polymers of the present invention can be melt processed by numerous methods to prepare a vast array of useful devices. These materials can be injection or compression molded to make implantable medical and surgical devices, including wound closure devices. The preferred devices are suture anchor devices, adhesion prevention films and hemostatic foam barriers.

Alternatively, the segmented polymers can be extruded to prepare fibers. The filaments thus produced may be fabricated into sutures or ligatures, attached to surgical needles, packaged, and sterilized by known techniques. The materials of the present invention may be spun as multifilament yarn and woven or knitted to form sponges or gauze, (or non-woven sheets may be prepared) or used in conjunction with other molded compressive structures such as prosthetic devices within the body of a human or animal where it is desirable that the structure have high tensile strength and desirable levels of compliance and/or ductility. Useful embodiments include tubes, including branched tubes, for artery, vein or intestinal repair, nerve splicing, tendon splicing, sheets for tying up and supporting damaged surface abrasions, particularly major abrasions, or areas where the skin and underlying tissues are damaged or surgically removed. Most especially, suture applications where monofilament suture with less tissue drag, lower modulus and short BSR profiles are needed. Most especially in plastic surgery applications, where shorter absorption times and better tissue pass through would lead to better tissue fixation and less scaring.

Additionally, the segmented polymers can be molded to form films which, when sterilized, are useful as adhesion prevention barriers.

In another embodiment of the present invention, the inventive polymers may also be used as coatings for sutures and the like to improve the knot strengths and the tiedown properties, as well as to reduce the tissue drag of sutures. Conventional coating procedures can be used to apply the coating to sutures. A preferred method of applying the coating is to continuously pull the suture to be coated through a solution containing in the range of from about 1 to about 20 weight percent polymer. The suture is pulled through the coating solution in a vertical direction to insure uniform drainage. The freshly coated fiber would then be pulled continuously through a drying tunnel, taken up on a wind-up wheel and vacuum dried overnight at room temperature.

This coating is ideally suited for applying to braided sutures, since braided sutures generally have chattery or rough tie-down properties. The coating may be applied to monofilament or braided absorbable or nonabsorbable sutures. Suitable absorbable sutures may be made from naturally derived materials including but not limited to catgut and collagen, or from synthetic absorbable materials including but not limited to homopolymers of glycolide, L-lactide, ε-caprolactone, and 1,4-dioxan-2-one and copolymers of glycolide, L-lactide, D,L-lactide, e-caprolactone, 1,3-dioxan-2-one, 1,4-dioxan-2-one, 1,5-dioxepan-2-one and 1,4-dioxepan-2-one. Suitable nonabsorbable sutures may be made from naturally occurring, nonabsorbable materials including but not limited to silk, cotton, and linen or synthetic nonabsorbable materials including but not limited to polyesters, polyamides (e.g., nylon, nylon 6, nylon 66 etc.), and polyolefins (e.g., polyethylene and polypropylene).

Sutures coated with the polymers of this invention are desirable because they have a more slippery feel, thus making it easier for the surgeon to slide a knot down the suture to the site of surgical trauma. In addition, the suture can be passed more easily through body tissue thereby reducing tissue trauma. These advantages are exhibited in comparison to sutures which do not have their surfaces coated with the polymer of this invention. In this particular application (suture coating), it may be advantageous to use polymers with low molecular weights including copolymers having inherent viscosities in the range of 0.15 dL/g to 0.75 dL/g in a 0.1 g/dL solution of HFIP at 25° C.

In another embodiment of the present invention, the polymers can be used to coat surgical needles in order to facilitate passage through tissue. The amount of coating applied to the surface of the needle is an amount which creates a layer with a thickness ranging preferably between about 2 to about 20 microns, more preferably between about 4 to about 8 microns. If the amount of coating on the needle were such that the thickness of the coating layer was greater than about 20 microns, or if the thickness was less than about 2 microns, then the desired performance of the needle as it is passed through tissue may not be achieved.

In another embodiment of the present invention, the polymers can be used as a drug delivery matrix. To form this matrix, the polymer would be mixed with a therapeutic agent. The variety of different therapeutic agents which can be used in conjunction with the polymers of the present invention is vast. In general, therapeutic agents which may be administered via the pharmaceutical compositions of the invention include, without limitation: antiinfectives such as antibiotics and antiviral agents; analgesics and analgesic combinations; anorexics; antihelmintics; antiarthritics; antiasthmatic agents; anticonvulsants; antidepressants; antidiuretic agents; antidiarrheals; antihistamines; antiinflammatory agents; antimigraine preparations; antinauseants; antineoplastics; antiparkinsonism drugs; antipruritics; antipsychotics; antipyretics, antispasmodics; anticholinergics; sympathomimetics; xanthine derivatives; cardiovascular preparations including calcium channel blockers and beta-blockers such as pindolol and antiarrhythmics; antihypertensives; diuretics; vasodilators including general coronary, peripheral and cerebral; central nervous system stimulants; cough and cold preparations, including decongestants; hormones such as estradiol and other steroids, including corticosteroids; hypnotics; immunosuppressives; muscle relaxants; parasympatholytics; psychostimulants; sedatives; and tranquilizers; and naturally derived or genetically engineered proteins, polysaccharides, glycoproteins, or lipoproteins.

The drug delivery matrix may be administered orally, parenterally, subcutaneously, vaginally or anally. Matrix formulations may be formulated by mixing one or more therapeutic agents with the polymer. The therapeutic agent, may be present as a liquid, a finely divided solid, or any other appropriate physical form. Typically, but optionally, the matrix will include one or more additives, such as diluents, carriers, excipients, stabilizers or the like.

The amount of therapeutic agent will depend on the particular drug being employed and medical condition being treated. Typically, the amount of drug represents about 0.001% to about 70%, more typically about 0.001% to about 50%, most typically about 0.001% to about 20% by weight of the matrix.

The quantity and type of polymer incorporated into the drug delivery matrix will vary depending on the release profile desired and the amount of drug employed. The product may contain blends of polymer to provide the required release profile or consistency to a given formulation.

Upon contact with body fluids, the polymer undergoes gradual degradation (mainly through hydrolysis) with concomitant release of the dispersed drug for a sustained or extended period. This can result in prolonged delivery (over, say 1 to 5,000 hours, preferably 2 to 800 hours) of effective amounts (say, 0.0001 mg/kg/hour to 10 mg/kg/hour) of the drug. This dosage form can be administered as is necessary depending on the subject being treated, the severity of the affliction, the judgment of the prescribing physician, and the like.

Individual formulations of drug and polymer may be tested in appropriate in vitro and in vivo models to achieve the desired drug release profile. For example, a drug could be formulated with a polymer and orally administered to an animal. The drug release profile could then be monitored by appropriate means such as, by taking blood samples at specific times and assaying the samples for drug concentration. Following this or similar procedures, those skilled in the art will be able to prepare a variety of formulations.

Furthermore, the segmented polymers of the present invention can be processed by conventional techniques to form foams, which are useful as hemostatic barriers, bone substitutes, and tissue scaffolds.

In more detail, the surgical and medical uses of the filaments, films, foams and molded articles of the present invention include, but are not necessarily limited to knitted products, woven or non-woven, and molded products including:

a. burn dressings b. hernia patches c. medicated dressings d. fascial substitutes e. gauze, fabric, sheet, felt or sponge for liver hemostasis f. gauze bandages g. arterial graft or substitutes h. bandages for skin surfaces i. burn dressings j. bone substitutes k. needles l. intrauterine devices m. draining or testing tubes or capillaries n. surgical instruments o. vascular implants or supports p. vertebral discs q. extracorporeal tubing for kidney and heart-lung machines r. artificial skin and others s. stents t. suture anchors u. injectable defect fillers v. preformed defect fillers w. tissue adhesives and sealants x. bone waxes y. cartilage replacements z. hemostatic barriers aa. tissue scaffolds bb. monofilament and braided sutures.

cc. suture knot clips dd. orthopedic pins, clamps, screws, and plates ee. clips (e.g., for vena cava)

ff. staples gg. hooks, buttons, and snaps

The following non-limiting examples are illustrative of the principles and practice of this invention. Numerous additional embodiments within the scope and spirit of the invention will become apparent to those skilled in the art.

EXAMPLES

The examples describe new segmented polymers composed of glycolide, ε-caprolactone, and trimethylene carbonate, potentially useful as biomedical devices. In these examples glycolide will be abbreviated as "Gly", ε-caprolactone as "Cap", trimethylene carbonate as "TMC", polyglycolide as "PGA", poly ε-caprolactone as "PCL" and poly trimethylene carbonate as "PTMC".

Example 1

This example describes the synthesis of a "triblock" copolymer of caprolactone/trimethylene carbonate and glycolide. The prepolymer was (Cap/TMC/Gly) and additional glycolide which is believed to provide end blocks of glycolide repeat units.

Copolymer synthesis:

Sample 1 was made using the following monomer charges (in mole percent) in a sequential polymerization:

1st stage (15/25/5) (Cap/TMC/Gly)

2nd stage 7.5+7.5=15 glycolide

3rd stage 20+20=40 glycolide

| Overall composition: | Cap/TMC/Gly |
|---|---|
| | 15/25/60 |

The polymer structure is believed to be substantially:

| Gly/Gly(Cap/TMC/Gly)/Gly/Gly |
|---|
| 20/7.5/(15/25/5)/7.5/20 |

(based on the mole percent of monomer charged into the reactor).

Into a reactor provided with stirrer and jacket with heating medium is charged 258.48 grams (2.226 moles) of glycolide, 1,135.71 grams (11.13 moles) of trimethylene carbonate, 762.53 grams (6.68 moles) of epsilon caprolactone, 3.13 mls. (0.0329 moles) of diethylene glycol and 2.08 mls of a 0.33 molar solution of stannous octoate in toluene. The reactor is put under vacuum and the vacuum is broken with nitrogen; the vacuum and nitrogen vacuum breaking step is repeated once more. The heating medium temperature is then raised to 195° C. and it is kept for two hours, 775.44 grams (6.68 moles) of molten glycolide are added and the reaction is continued for 35 minutes. Then 2,067.84 grams (17.815 moles) of molten glycolide are added and the heating medium temperature is increased to 204° C. The reaction is exothermic and the batch temperature surpasses the heating medium temperature. This event is designated as the exotherm crossover. The reaction is terminated 55 minutes after the exotherm crossover. The copolymer is discharged, and upon cooling it is ground and dried. The drying is done under vacuum for 18 hours at room temperature and then for 24 hours at 110° C. The mole percent composition of the polymer by H NMR analysis was:

| PGA | Glycolide | PTMC | TMC | PCL | Cap |
|---|---|---|---|---|---|
| 61.5 | <0.1 | 23.9 | <0.1 | 14.5 | <0.1 |

The molecular weight Mw of the polymer was 59,000. The melting point by DSC was 213° C. The heat of fusion was 28 J/g; hot stage microscopy revealed that the majority of the sample crystallized at 170°–174° C.

Example 2

This Example describes the preparation of a copolymer which contains no glycolide in the prepolymer.

Copolymer Synthesis:

Sample 2 was made using the following monomer charges (in mole percent) in a sequential polymerization:

1st stage (15/25) (Cap/TMC)

2nd stage 15 glycolide

3rd stage 45 glycolide

| Overall composition: | Cap/TMC/Gly |
|---|---|
| | 15/25/60 |

The polymer structure is believed to be substantially:

| Gly/Gly(Cap/TMC)/Gly/Gly |
|---|
| 22.5/7.5/(15/25)/7.5/22.5 |

(based on the mole percent of monomer charged into the reactor).

Into a reactor provided with stirrer and jacket with heating medium is charged 1,135.71 grams (11.13 moles) of trimethylene carbonate, 762.53 grams (6.68 moles) of epsilon caprolactone, 3.13 mls. (0.0329 moles) of diethylene glycol and 2.08 mls of a 0.33 molar solution of stannous octoate in toluene. The reactor is put under vacuum and the vacuum is broken with nitrogen; the vacuum and nitrogen vacuum breaking step is repeated once more. The heating medium temperature is raised to 195° C. and it is kept for two hours, 775.44 grams (6.68 moles) of molten glycolide are added and reaction is continued for 35 minutes. Then 2,326.32 grams of molten glycolide are added and the heating medium temperature is increased to 204° C. The reaction is exothermic and the batch temperature surpasses the heating medium temperature. This event is designated as the exotherm crossover. The reaction is terminated 55 minutes after the exotherm crossover. The copolymer is discharged, and upon cooling it is ground and dried. The drying is done under vacuum for 18 hours at room temperature and then for 24 hours at 110° C. The mole percent composition of the polymer by H NMR analysis was:

| PGA | Glycolide | PTMC | TMC | PCL | Cap |
|---|---|---|---|---|---|
| 61.7 | 0.8 | 23.6 | 0.0 | 13.9 | <0.1 |

The molecular weight Mw of the polymer was 64,000.

Example 3

The copolymers from Examples 1 and 2 were extruded into monofilament under the following conditions to compare copolymer properties.
Effect of Center Segment Glycolide Content

| Sample No. | 1 | 2 |
|---|---|---|
| Composition | Gly/Gly/(Cap/TMC/Gly)/Gly/Gly | Gly/Gly(Cap/TMC)Gly/Gly |
| Mole Percent | 20/7.5(15/25/5)7.5/20 | 22.5/7.5(15/25)7.5/22.5 |

Extrusion

The copolymers were extruded into a monofilament suture generally as follows:

TABLE I

| | Extrusion | | |
|---|---|---|---|
| Sample No. | 1 | 2A | 2B/C |
| Ram Speed, cm/min | 2 | 2 | 2 |
| Shear Rate, (1/sec) | 212.6 | 212.6 | 212.6 |
| Packing Temp., °C. | 150 | 160 | 160 |
| Run Temperature | 220 | 230 | 230 |
| App Visc., Poise | 3,653 | 3,975 | 3,008 |
| Residence Time, sec. | 660 | 700 | 700 |
| Bath conditions | ice water | ice water | ice water |
| Take Up (ft/min) | 24 | 24 | 24 |

The copolymers were then drawn under the conditions described below.

TABLE II

| | Orientation | | | |
|---|---|---|---|---|
| Sample No. | 1 | 2A | 2B | 2C |
| Draw Input speed, ft/min | 4 | 4 | 4 | 4 |
| 1st Draw Ratio/temp. °C. | 5/56 | 5/55 | 5/55 | 5 |
| Output speed, ft/min | 20 | 20 | 20 | 20 |

TABLE II-continued

| | Orientation | | | |
|---|---|---|---|---|
| Sample No. | 1 | 2A | 2B | 2C |
| 2nd Draw Ratio/temp. °C. | 1.3/75 | 1.5/75 | 1.2/75 | 1.1/75 |
| Overall Draw Ratio | 6.5 | 7.5 | 6 | 5.5 |

Fiber Properties

The characteristic properties of the sutures of the invention are readily determined by conventional test procedures. The tensile properties (i.e., straight and knot tensile strengths and elongation) displayed herein were determined with an INSTRON tensile tester. The settings used to determine the straight tensile, knot tensile and break elongation were the following:

TABLE III

| | GAUGE LENGTH (cm) | CHART SPEED (cm/min) | CROSSHEAD SPEED (cm/min) |
|---|---|---|---|
| STRAIGHT TENSILE | 12.7 | 30.5 | 30.5 |
| KNOT TENSILE | 12.7 | 30.5 | 30.5 |
| BREAK ELONGATION | 12.7 | 30.5 | 30.5 |

The straight tensile strength is calculated by dividing the force to break by the initial cross-sectional area of the suture.

The elongation at break is read directly from the stress-strain curve of the sample.

The knot tensile strength of a suture is determined in separate tests. The surgeon's knot is a square knot in which the free end is first passed twice, instead of once, though the loop, and the ends drawn taut so that a single knot is superimposed upon a compound knot. The first knot is started with the left end over the right end and sufficient tension is exerted to tie the knot securely.

The specimen is placed in the INSTRON tensile tester with the knot approximately midway between the clamps. The knot tensile strength is calculated by dividing the force required to break by the initial cross-sectional area of the fiber. The tensile strength values are reported as KPSI (1KPSI=1,000 PSI).

The results of testing Samples 1 and 2 that were produced by the process described above are provided below. As can be seen from the data although Sample 1 and Sample 2 may have similar tensile and knot strengths, the Young's Modulus values for the Samples are very different.

TABLE IV

| Sample No. | 1 | 2A | 2B | 2C |
|---|---|---|---|---|
| Av. Diameter, mils | 7.6 | 6.4 | 7.7 | 7.9 |
| Straight tens, lbs | 4.66 | 3.2 | 3.18 | 3.31 |
| Knot tens. lbs | 2.74 | 2.2 | 3.12 | 2.99 |
| Str. tensile, kpsi | 102.72 | 99.5 | 67.98 | 67.17 |

TABLE IV-continued

| Sample No. | 1 | 2A | 2B | 2C |
|---|---|---|---|---|
| Knot tensile, kpsi | 60.39 | 63.9 | 66.69 | 60.77 |
| Percent elongation | 58 | 11.8 | 41 | 55.5 |
| Modulus, Kpsi | 144 | 1,712 | 1,027 | 942 |

The higher draw ratios for Sample 2A produced a more oriented fiber with a higher Young's modulus and a lower percent elongation (relative to the other Sample 2 fibers). The lower draw ratios used in Sample 2C produced a less oriented fiber with a lower Young's Modulus and lower tensile strength and higher percent elongation (again relative to the other Sample 2 fibers). Sample 1 however, provides a significantly reduced Young's Modulus when compared to all the Sample 2 fibers produced using the different drawing conditions.

Example 4

This Example describes the preparation of a copolymer which contains no ε-caprolactone in the prepolymer.
Copolymer Synthesis:
    Sample 3 was made using the following monomer charges (in mole percent) in a sequential polymerization:
    1st stage (39.23/5.77) (TMC/Gly)
    2nd stage 55 glycolide

| Overall composition: | (TMC/Gly)Gly (39.23/5.77)55 |
|---|---|

The polymer structure is believed to be substantially:

| Gly(TMC/Gly)/Gly 27.5/(39.23/5.77)27.5 |
|---|

(based on the mole percent of monomer charged into the reactor).

Into a reactor provided with stirrer and jacket with heating medium is charged 1,809.83 grams (17.743 moles) of trimethylene carbonate, 302.86 grams (2.609 moles) of glycolide, 3.18 mls. of diethylene glycol and 2.11 mls of a 0.33 molar solution of stannous octoate in toluene. The reactor is put under vacuum and the vacuum is broken with nitrogen; the vacuum and nitrogen vacuum breaking step is repeated once more. The heating medium temperature is raised to 185° C. and it is kept for three hours, 2,887.31 grams (24.875 moles) of molten glycolide are added and the heating medium temperature is increased to 202° C. The reaction is exothermic and the batch temperature surpasses the heating medium temperature. This event is designated as the exotherm crossover. The reaction is terminated 55 minutes after the exotherm crossover. The copolymer is discharged, and upon cooling it is ground and dried. The drying is done under vacuum for 18 hours at room temperature and then for 24 hours at 110° C. The mole percent composition of the polymer by NMR analysis was:
    61.6% PGA and 38.4% PTMC Example 5

This Example describes the preparation of a copolymer which contains no trimethylene carbonate in the prepolymer.
Copolymer Synthesis:
    Sample 4 was made using the following monomer charges (in mole percent) in a sequential polymerization:
    1st stage (39.23/5.77) (Cap/Gly)
    2nd stage 55 glycolide

| Overall composition: | (Cap/Gly)Gly (39.28/5.72)55 |
|---|---|

The polymer structure is believed to be substantially:

| Gly(Cap/Gly)/Gly 27.5/(39.28/5.72)27.5 |
|---|

(based on the mole percent of monomer charged into the reactor).

Into a reactor provided with stirrer and jacket with heating medium is charged 1,943.85 grams (17.03 moles) of epsilon caprolactone, 288.05 grams (2.4816 moles) of glycolide, 3.05 mls. of diethylene glycol and 2.02 mls of a 0.33 molar solution of stannous octoate in toluene. The reactor is put under vacuum and the vacuum is broken with nitrogen; the vacuum and nitrogen vacuum breaking step is repeated once more. The heating medium temperature is raised to 185° C. and it is kept for three hours, 2,768.1 grams (23.848 moles) of molten glycolide are added and the heating medium temperature is increased to 202° C. The reaction is exothermic and the batch temperature surpasses the heating medium temperature. This event is designated as the exotherm crossover. The reaction is terminated 55 minutes after the exotherm crossover. The copolymer is discharged, and upon cooling it is ground and dried. The drying is done under vacuum for 18 hours at room temperature and then for 24 hours at 110° C. The mole percent composition of the polymer by NMR was:
    PGA 60.5%, PCL 39.5%

Example 6

The copolymers from Examples 4 and 5 were extruded into monofilament under the following conditions to compare copolymer properties. The testing of the copolymers from Example 4 and 5 were performed as described in Example 3.

Extrusion and orientation details for the two polymers are given below:

TABLE V

| Sample No. | 3 | | 4 |
|---|---|---|---|
| Composition | (TMC/Gly)Gly (39.23/5.11/77)55 | | (Cap/Gly)Gly (39.27/5.72)55 |
| Extrusion | | | |
| Ram Speed, cm/min | 2 | | 2 |
| Shear Rate, (1/sec) | 212.6 | | 212.6 |
| Packing Temp., °C. | 150 | | 150 |
| Run Temperature | 200 | | 225 |
| App Visc., Poise | 6178 | | |
| Residence Time, sec. | 550 | | 750 |
| Bath conditions | ice water | | ice water |
| Take Up (ft/min) | 24 | | 24 |
| Sample No. | 3A | 3B | 3C |
| Orientation | | | |
| Draw Input speed, ft/min | 4 | 4 | 4 |
| 1st Draw Ratio/temp. C. | 5/55 | 5/55 | 5/55 |
| Output speed, ft/min | 20 | 20 | 20 |

TABLE V-continued

| | | | |
|---|---|---|---|
| 2nd Draw Ratio/temp. °C. | 1.2/75 | 1.5/75 | 1.4/75 |
| Overall Draw Ratio | 6.5 | 7.5 | 7 |
| Fiber Properties | | | |
| Av. Diameter, mils | 6.98 | 7.14 | 7.38 |
| Straight tens, lbs | 0.765 | 0.719 | 0.944 |
| Knot tens, lbs | 0.473 | 0.392 | 0.544 |
| Str. tensile, kpsi | 20.028 | 17.97 | 22.1 |
| Knot tensile, kpsi | 12.37 | 9.8 | 12.72 |
| % elongation | 14.74 | 14.42 | 17.64 |

The above examples clearly show the advantage of the copolymers prepared with center block composition consisting of the terpolymer of Caprolactone/TMC and Glycolide with tail ends of PGA. The fibers produced unexpectedly superior properties than those obtained with the copolymers with center block of caprolactone/TMC or those with center block of TMC/glycolide or center block of Caprolactone/glycolide.

Example 7

The following example provides additional Samples of the inventive polymer made as described in Example 1 with the following compositions:

Sample 5

| Composition: | Gly/Gly/(Cap/TMC/Gly)/Gly/Gly |
|---|---|
| | 20/6/(26/10/12)/6/20 |

1st stage (26/10/12) (Cap/TMC/Gly)
2nd stage 12 glycolide
3rd stage 40 glycolide Sample 6

| Composition: | Gly/Gly/(Cap/TMC/Gly)/Gly/Gly |
|---|---|
| | 20/6/(16/20/12)/6/20 |

1st stage (16/20/12) (Cap/TMC/Gly)
2nd stage 12 glycolide
3rd stage 40 glycolide Sample 7

| Composition: | Gly/Gly/(Cap/TMC/Gly)/Gly/Gly |
|---|---|
| | 20/7.5/(20/10/15)/7.5/20 |

1st stage (20/10/15) (Cap/TMC/Gly)
2nd stage 15 glycolide
3rd stage 40 glycolide Reaction conditions for the three polymers are summarized in Table I:

TABLE VI

| Sample No. | 5 | 6 | 7 |
|---|---|---|---|
| Composition | (Cap/TMC/Gly) | (Cap/TMC/Gly) | (Cap/TMC/Gly) |
| | Gly/Gly | Gly/Gly | Gly/Gly |
| Composition mole percent | (26/10/12) 12/40 | (16/20/12) 12/40 | (20/10/15) 15/40 |
| Overall Composition | Cap/TMC/Gly 26/10/64 | Cap/TMC/Gly 16/20/64 | Cap/TMC/Gly 20/10/70 |

TABLE VI-continued

| Sample No. | 5 | 6 | 7 |
|---|---|---|---|
| Cap grams | 1,169.77 | 845.6 | 978.81 |
| TMC grams | 402.06 | 944.61 | 437.35 |
| 1st Gly, g. | 549.03 | 644.96 | 746.54 |
| 2nd Gly, g. | 549.03 | 644.96 | 746.54 |
| 3rd Gly, g. | 1830.11 | 2149.85 | 1990.76 |
| DEG, mls | 2.77 | 3.26 | 3.01 |
| cat. mls | 1.84 | 2.16 | 2.0 |
| 1st stage hrs/Deg. C. | 3/180 | 3/180 | 2.5/180 |
| 2nd stage min/deg. C. | 20/180 | 20/180 | 20/180 |
| 3rd stage Exo + min./C. | 50/205 | 50/202 | 35/203 |

The overall mole percent composition of the dried copolymers as determined by H NMR are given in Table II:

TABLE VII

| Sample No | PGA | GL | PCL | CAP | PTMC | TMC |
|---|---|---|---|---|---|---|
| Sample 5 | 64.4 | 0.0 | 26 | .1 | 9.6 | 0.0 |
| Sample 6 | 63.8 | 0.6 | 16 | <0.1. | 19.4 | 0.2 |
| Sample 7 | 69.4 | 0.6 | 19.7 | <0.1 | 10.1 | 0.1 |

TABLE VIII

| Sample No. | Mw | Mn | Tm, °C. | H, J/g. | IV, dl/g |
|---|---|---|---|---|---|
| Sample 5 | 86,000 | 24,000 | 208 | 37 | 1.56 |
| Sample 6 | 89,000 | 26,000 | 191 | 33 | 1.5 |
| Sample 7 | 89,000 | 24,000 | | | 1.82 |

The polymers were extruded into size 4-0 sutures using a two step extrusion/orientation process as described in Table IX. They exhibit outstanding properties.

The in vitro strength retention of unannealed and annealed size 4-0 sutures with annealing conditions designated with notation (percent relaxation/degrees C./hours) are given in Table X the bath was at 40.9° C. and pH buffer of 7.0.

TABLE IX

| Sample No. | 5 | 6 | 7 |
|---|---|---|---|
| Extrusion | | | |
| Ram Speed, cm/min | 2 | 2 | 2 |
| Shear Rate, (1/sec) | 212.6 | 212.6 | 212.6 |
| Packing Temp., °C. | 170 | 160 | 170 |
| Run Temperature | 230 | 220 | 235 |
| App Visc., Poise | 4,942 | 5,479 | 5,533 |
| Residence Time, sec. | 600 | 615 | 630 |
| Bath conditions | ice water | ice water | ice water |
| Take Up (ft/min) | 24 | 24 | 24 |

The copolymers were then drawn under the conditions described below.

| | | | |
|---|---|---|---|
| Orientation | | | |
| Draw Input Speed, ft/min | 4 | 4 | 4 |
| 1st Draw Ratio/temp. °C. | 5/45 | 5/45 | 5/45 |
| Output Speed, ft/min | 20 | 20 | 20 |
| 2nd Draw Ratio/temp °C. | 1.3/65 | 1.3/65 | 1.3/65 |
| Overall Draw Ratio | 6.5 | 6.5 | 6.5 |
| Fiber Properties | | | |
| Diameter mils | 7.6 | 7.8 | 7.9 |
| Straight Break Strength, lbs. | 4.8 | 5.1 | 5.2 |
| Knot Break Strength, lbs | 3.9 | 3.5 | 4.1 |
| Straight Tensile, Kpsi | 99.7 | 107.8 | 106.0 |
| Knot Tensile, Kpsi | 85.3 | 74.1 | 83.1 |

TABLE IX-continued

| Sample No. | 5 | 6 | 7 |
|---|---|---|---|
| w/o Elongation | 45.0 | 49.8 | 48.2 |
| Modulus, Kpsi | 84.7 | 33.7 | 74.4 |

TABLE X

| fibers from copolymers | 0 day straight tensile. lbs | 12 day straight tens. lbs | BSR % |
|---|---|---|---|
| Sample 5 | | | |
| unannealed | 3.939 | 2.18 | 55 |
| annealed (5/90/6) | 4.53 | | |
| Sample 6 | | | |
| unannealed | 4.68 | 3.36 | 71.8 |
| Sample 7 | | | |
| unannealed | 4.93 | 3.01 | 61 |
| annealed (0/90/6) | 5.46 | 3.3 | 60 |

We claim:

1. An absorbable, biocompatible segmented copolymer comprising:
 a prepolymer containing repeating units obtained from trimethylene carbonate, glycolide and ε-caprolactone monomers, wherein the mole percent of trimethylene carbonate is in the range of from about 2 to about 40; the mole percent of glycolide is in the range of from about 2 to about 55 mole percent and the mole percent of ε-caprolactone is in the range of from about 2 to about 40 mole percent;
 copolymerized with in the range of from about 10 mole percent to about 80 mole percent of repeating units of glycolide; wherein the mole percentages are based on the total moles of monomer in the segmented copolymer.

2. The segmented copolymer of claim 1 wherein the copolymer has an inherent viscosity is from about 1.0 dL/g to about 3.0 dL/g as measured in HFIP at a concentration of 0.1 g/dL.

3. The segmented copolymer of claim 1 wherein the segmented copolymer contains about 40 mole percent to about 80 mole percent of glycolide.

4. The segmented copolymer of claim 1 wherein the prepolymer contains in the range of from about 10 to about 30 mole percent, trimethylene carbonate repeating units.

5. The segmented copolymer of claim 1 wherein the prepolymer contains in the range of from about 5 to about 15 mole percent glycolide repeating units.

6. The segmented copolymer of claim 5 wherein the repeating units of ε-caprolactone in the prepolymer comprise in the range of from about 10 mole percent to about 30 mole percent of the segmented copolymer.

7. An absorbable medical device formed from an absorbable, biocompatible segmented copolymer comprising:
 a prepolymer containing repeating units obtained from trimethylene carbonate, glycolide and ε-caprolactone monomers, wherein the mole percent of trimethylene carbonate is in the range of from about 2 to about 40; the mole percent of glycolide is in the range of from about 2 to about 55 mole percent and the mole percent of ε-caprolactone is in the range of from about 2 to about 40 mole percent;
 copolymerized with in the range of from about 10 mole percent to about 80 mole percent of repeating units of glycolide; wherein the mole percentages are based on the total moles.

8. An absorbable medical device of claim 7 wherein the prepolymer contains in the range of from about 5 to about 15 mole percent glycolide.

9. The absorbable medical device of claim 8 wherein the segmented copolymer contains in the range of from about 10 mole percent to about 30 mole percent of repeating units of trimethylene carbonate; and in the range of from about 10 mole percent to about 30 mole percent of repeating units of ε-caprolactone.

10. The absorbable medical device of claim 7 wherein the medical device is selected from the group consisting of burn dressings, hernia patches, medicated dressings, fascial substitutes, gauze, fabric, sheet, felt, sponge for liver hemostasis, gauze bandages, arterial graft or substitutes, bandages for skin surfaces, burn dressings, bone substitutes, needles, intrauterine devices, tubes, surgical instruments, vascular implants, vascular supports, vertebral discs, extracorporeal tubing, artificial skin, stents, suture anchors, injectable defect fillers, preformed defect fillers, tissue adhesives, tissue sealants, bone waxes, cartilage replacements, hemostatic barriers, tissue scaffolds, monofilament sutures and braided sutures.

11. A medical device coated with a segmented copolymer comprising:
 a prepolymer containing repeating units of trimethylene carbonate, glycolide and ε-caprolactone, wherein the mole percent of trimethylene carbonate is in the range of from about 2 to about 40; the mole percent of glycolide is in the range of from about 2 to about 55 mole percent and the mole percent of ε-caprolactone is in the range of from about 2 to about 40 mole percent;
 copolymerized with in the range of from about 10 mole percent to about 80 mole percent of glycolide; wherein the mole percentages are based on the total moles of monomer in the segmented copolymer.

12. The medical device of claim 11 wherein the medical device is a suture.

13. The medical device of claim 11 wherein the medical device is a needle.

14. A drug delivery matrix comprising a drug and a segmented polymer formed from:
 a prepolymer containing repeating units of trimethylene carbonate, glycolide and ε-caprolactone, wherein the mole percent of trimethylene carbonate is in the range of from about 2 to about 40; the mole percent of glycolide is in the range of from about 2 to about 55 mole percent and the mole percent of ε-caprolactone is in the range of from about 2 to about 40 mole percent;
 copolymerized with in the range of from about 10 mole percent to about 80 mole percent of glycolide; wherein the mole percentages are based on the total moles of monomer in the segmented copolymer.

* * * * *